(12) United States Patent
Novy et al.

(10) Patent No.: US 6,589,783 B2
(45) Date of Patent: *Jul. 8, 2003

(54) MULTIPLE HOST EXPRESSION VECTOR

(75) Inventors: Robert E. Novy, Verona, WI (US); Scott A. Monsma, Madison, WI (US)

(73) Assignee: Novagen, Inc., Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/548,880

(22) Filed: Apr. 13, 2000

(65) Prior Publication Data

US 2002/0160507 A1 Oct. 31, 2002

(51) Int. Cl.[7] .................. C12N 15/00; C12N 15/09; C12N 15/65; C07H 21/00; C07H 21/04
(52) U.S. Cl. .................. 435/320.1; 536/23.1; 536/24.1
(58) Field of Search .................. 536/23.1, 24.1; 435/320.1

(56) References Cited

U.S. PATENT DOCUMENTS 6,194,158 B1 * 2/2001 Kroes et al. .................. 435/6

OTHER PUBLICATIONS pDual Expression System, Stratagene on–line catalog, http://www.stratagene.com/vectors/expression/pdual.htm; Mar. 23, 2001.*

Novy et al. FASEB Journal 13(7):A1552, abstract# 1269, Apr. 1999.*

Novy et al. Mol. Biol. Cell 10(Suppl):270a, abstract#1562, Nov. 1999.*

Hasnain et al. Gene 190:113–118 1997.*

Binder et al. Plant Mol. Biol. 32:303–314 1996.*

Romanos et al. Yeast 8:423–488 1992.* pBAC–2cp Transfer Plasmid, Novagen Catalog p. TB128 1/96.

pcDNA3.1/Hygro Vectors, Invitrogen abstract.

pCI Vector Circle Map, Sequence and Restriction Sites, Abstract 9/94.

pDual Expression System, Statagen Catalog (Aug. 9, 1999).

pET–28a–c(+) Vectors, Novagen Catalog p. TB074 12/98.

* cited by examiner

Primary Examiner—David Guzo
Assistant Examiner—David A. Lambertson
(74) Attorney, Agent, or Firm—Quarles & Brady LLP

(57) ABSTRACT

A triple host vector is described which is capable of expressing an inserted protein coding DNA sequence in any of three distinct host systems. The vector includes three promoters, one each for vertebrate, bacterial and insect host cells, so that the protein coding sequence can be cloned into the vector once and the vector can be used to express protein in all three types of host cells. The arrangement and selection of the promoters contributes to expression characteristics in all three host systems that is comparable to single host expression vectors.

9 Claims, 6 Drawing Sheets

B) Tandem head-to-tail promoters in which the upstream promoter creates a transcript encoding exon/intron splice sites flanking the downstream promoters.,

SEQUENCE LISTING

<160> NUMBER OF SEQ ID NOS: 1

<210> SEQ ID NO 1
<211> LENGTH: 5756
<212> TYPE: DNA
<213> ORGANISM: Artificial Sequence
<220> FEATURE:
<223> OTHER INFORMATION: Description of Artificial Sequence: Expression
      vector

<400> SEQUENCE: 1

```
tcctgcatct tttaatcaaa tcccaagatg tgtataaacc accaaactgc caaaaaatga      60
aaactgtcga caagctctgt ccgtttgctg gcaactgcaa gggtctcaat cctatttgta     120
attattgaat aataaaacaa ttataaatgc taaatttgtt ttttattaac gatacaaacc     180
aaacgcaaca agaacatttg tagtattatc tataattgaa aacgcgtagt tataatcgct     240
gaggtaatat ttaaaatcat tttcaaatga ttcacagtta atttgcgaca atataatttt     300
attttcacat aaactagacg ccttgtcgtc ttcttcttcg tattccttct cttttttcatt    360 tttctcttca taaaaattaa catagttatt atcgtatcca tatatgtatc tatcgtatag     420
agtaaatttt ttgttgtcat aaatatatat gtctttttta atggggtgta tagtaccgct     480
gcgcatagtt tttctgtaat ttacaacagt gctattttct ggtagttctt cggagtgtgt     540
tgctttaatt attaaattta tataatcaat gaatttggga tcgtcggttt tgtacaatat     600
gttgccggca tagtacgcag cttcttctag ttcaattaca ccattttta gcagcaccgg      660 attaacataa ctttccaaaa tgttgtacga accgttaaac aaaaacagtt cacctccctt     720
ttctatacta ttgtctgcga gcagttgttt gttgttaaaa ataacagcca ttgtaatgag     780
acgcacaaac taatatcaca aactggaaat gtctatcaat atatagttgc tctagttatt     840
aatagtaatc aattacgggg tcattagttc atagcccata tatggagttc cgcgttacat     900
aacttacggt aaatggcccg cctggctgac cgcccaacga ccccgccca ttgacgtcaa      960 taatgacgta tgttcccata gtaacgccaa tagggacttt ccattgacgt caatgggtgg    1020
actatttacg gtaaactgcc cacttggcag tacatcaagt gtatcatatg ccaagtacgc    1080 ccctattga cgtcaatgac ggtaaatggc ccgcctggca ttatgcccag tacatgacct     1140
```

-continued

```
tatgggactt tcctacttgg cagtacatct acgtattagt catcgctatt accatgcatg    1200
gtcgaggtga gccccacgtt ctgcttcact ctccccatct ccccccctc cccaccccca    1260 attttgtatt tatttatttt ttaattattt tgtgcagcga tggggcggg gggggggggg    1320 gggcgcgcgc caggcggggc ggggcggggc gaggggcggg gcgggcgag gcggagaggt    1380 gcggcggcag ccaatcagag cggcgcgctc cgaaagtttc cttttatggc gaggcggcgg    1440
cggcggcggc cctataaaaa gcgaagcgcg cggcgggcgg gagtcgctgc gcgctgcctt    1500
cgccccgtgc cccgctccgc cgccgcctcg cgccgcccgc cccggctctg actgaccgcg    1560
ttactcccac aggtgagcgg gcgggacggc ccttctcctt cgggctgtaa ttagcgcttg    1620
gtttaatgac ggcttgtttc ttttctgtgg ctgcgtgaaa gccttgaggg gctccgggag    1680
ggccctttgt gcggggggag cggctcgggg ctgtccgcgg ggggacggct gccttcgggg    1740
gggacggggc agggcgggt tcggcttctg gcgtgtgacc ggcggctcta gagcctctgc    1800
taaccatgtt catgccttct tcttttcct acagctcctg ggcaacgtgc tggttattgt    1860
gctgtctcat cattttggca aagaattgga tcggaccgaa attaatacga ctcactatag    1920
gggaattgtg agcggataac aattccccgg agttaatccg ggacctttaa ttcaacccaa    1980
cacaatatat tatagttaaa taagaattat tatcaaatca tttgtatatt aattaaaata    2040
ctatactgta aattacattt tatttacaat caaaggagat ataccatggc gatatcccgg    2100
gagctcgtgg atccgaattc tcagatctcg gcgcgcctgc aggtcgacgg taccggttcg    2160
aagcttgcgc ccgcacagct gtatacacgt gcaagccagc cagaactcgc cccggaagac    2220
cccgaggatc tcgagcacca ccatcaccat caccatcact aagtgattaa cctcaggtgc    2280
aggctgccta tcagaaggtg gtggctggtg tggccaatgc cctggctcac aaataccact    2340
gagatcgatc ttttcccctc tgccaaaaat tatggggaca tcatgaagcc ccttgagcat    2400
ctgacttctg gctaataaag gaaatttatt ttcattgcaa tagtgtgttg gaattttttg    2460
tgtctctcac tcggaaggac atatgggagg gcaaatcatt taaaacatca gaatgagtat    2520
ttggtttaga gtttggcaac atatgccat atgtaactag cataacccct tggggcctct    2580
aaacgggtct tgagggtttt tttgctgaaa gcatgcggag gaaattctcc ttgaagtttc    2640
cctggtgttc aaagtaaagg agtttgcacc agacgcacct ctgttcactg gtccggcgta    2700
ttaaaacacg atacattgtt attagtacat ttattaagcg ctagattctg tgcgttgttg    2760
atttacagac aattgttgta cgtattttaa taattcatta aatttataat ctttagggtg    2820
gtatgttaga gcgaaaatca aatgattttc agcgtcttta tatctgaatt taaatattaa    2880
atcctcaata gatttgtaaa ataggtttcg attagtttca aacaagggtt gttttttccga    2940 accgatggct ggactatcta atggattttc gctcaacgcc acaaaacttg ccaaatcttg    3000
tagcagcaat ctagctttgt cgatattcgt ttgtgttttg ttttgtaata aaggttcgac    3060
gtcgttcaaa atattatgcg cttttgtatt tctttcatca ctgtcgttag tgtacaattg    3120
actcgacgta aacacgttaa atagagcttg gacatattta acatcgggcg tgttagcttt    3180
attaggccga ttatcgtcgt cgtcccaacc ctcgtcgtta gaagttgctt ccgaagacga    3240
ttttgccata gccacacgac gcctattaat tgtgtcggct aacacgtccg cgatcaaatt    3300
tgtagttgag ctttttggaa ttatttctga ttgcgggcgt ttttgggcgg gtttcaatct    3360
aactgtgccc gatttaatt cagacaacac gttagaaagc gatggtgcag gcggtggtaa    3420
catttcagac ggcaaatcta ctaatggcgg cggtggtgga gctgatgata aatctaccat    3480
cggtggaggc gcaggcgggg ctggcggcgg aggcggaggc ggaggtggtg gcggtgatgc    3540
```

-continued

```
agacggcggt ttaggctcaa atgtctcttt aggcaacaca gtcggcacct caactattgt    3600
actggtttcg ggcgccgttt ttggtttgac cggtctgaga cgagtgcgat ttttttcgtt    3660
tctaatagct tccaacaatt gttgtctgtc gtctaaaggt gcagcgggtt gaggttccgt    3720
cggcattggt ggagcgggcg gcaattcaga catcgatggt ggtggtggtg gtggaggcgc    3780
tggaatgtta ggcacgggag aaggtggtgg cggcggtgcc gccggtataa tttgttctgg    3840
tttagtttgt tcgcgcacga ttgtgggcac cggcgcaggc gccgctggct gcacaacgga    3900
aggtcgtctg cttcgaggca gcgcttgggg tggtggcaat tcaatattat aattggaata    3960
caaatcgtaa aaatctgcta taagcattgt aatttcgcta tcgtttaccg tgccgatatt    4020
taacaaccgc tcaatgtaag caattgtatt gtaaagagat tgtctcaagc tcggaacgct    4080
gcgctcggtc gttcggctgc ggcgagcggt atcagctcac tcaaaggcgg taatacggtt    4140
atccacagaa tcagggata acgcaggaaa gaacatgtga gcaaaaggcc agcaaaaggc    4200
caggaaccgt aaaaaggccg cgttgctggc gttttccat aggctccgcc ccctgacgag     4260
catcacaaaa atcgacgctc aagtcagagg tggcgaaacc cgacaggact ataaagatac    4320
caggcgtttc ccctggaag ctccctcgtg cgctctcctg ttccgaccct gccgcttacc      4380
ggatacctgt ccgcctttct cccttcggga agcgtggcgc tttctcaatg ctcacgctgt    4440
aggtatctca gttcggtgta ggtcgttcgc tccaagctgg gctgtgtgca cgaacccccc    4500
gttcagcccg accgctgcgc cttatccggt aactatcgtc ttgagtccaa cccggtaaga    4560
cacgacttat cgccactggc agcagccact ggtaacagga ttagcagagc gaggtatgta    4620
ggcggtgcta cagagttctt gaagtggtgg cctaactacg gctacactag aaggacagta    4680
tttggtatct gcgctctgct gaagccagtt accttcggaa aaagagttgg tagctcttga    4740
tccggcaaac aaaccaccgc tggtagcggt ggtttttttg tttgcaagca gcagattacg    4800
cgcagaaaaa aaggatctca agaagatcct ttgttaccaa tgcttaatca gtgaggcacc    4860
tatctcagcg atctgtctat ttcgttcatc catagttgcc tgactccccg tcgtgtagat    4920
aactacgata cgggagggct taccatctgg ccccagtgct gcaatgatac cgcgagaccc    4980
acgctcaccg gctccagatt tatcagcaat aaaccagcca gccggaaggg ccgagcgcag    5040
aagtggtcct gcaactttat ccgcctccat ccagtctatt aattgttgcc gggaagctag    5100
agtaagtagt tcgccagtta atagtttgcg caacgttgtt gccattgcta caggcatcgt    5160
ggtgtcacgc tcgtcgtttg gtatggcttc attcagctcc ggttcccaac gatcaaggcg    5220
agttacatga tcccccatgt tgtgcaaaaa agcggttagc tccttcggtc ctccgatcgt    5280
tgtcagaagt aagttggccg cagtgttatc actcatggtt atggcagcac tgcataattc    5340
tcttactgtc atgccatccg taagatgctt ttctgtgact ggtgagtact caaccaagtc    5400
attctgagaa tagtgtatgc ggcgaccgag ttgctcttgc ccggcgtcaa tacgggataa    5460
taccgcgcca catagcagaa ctttaaaagt gctcatcatt ggaaaacgtt cttcggggcg    5520
aaaactctca aggatcttac cgctgttgag atccagttcg atgtaaccca ctcgtgcacc    5580
caactgatct tcagcatctt ttactttcac cagcgtttct gggtgagcaa aaacaggaag    5640
gcaaaatgcc gcaaaaaagg gaataagggc gacacggaaa tgttgaatac tcatactctt    5700
cctttttcaa tattattgaa gcatttatca gggttattgt ctcatgtccg cgcgtt         5756
```

MULTIPLE HOST EXPRESSION VECTOR

CROSS-REFERENCE TO RELATED APPLICATIONS

STATEMENT REGARDING FEDERALLY SPONSORED RESEARCH OR DEVELOPMENT

BACKGROUND OF THE INVENTION

In the practice of modem biotechnology it has become common practice to create artificial gene constructions which are capable of expressing a foreign protein in a host which normally does not produce that protein. The process of producing a protein from a gene in a host is referred to as protein expression.

Interest in expressing proteins in foreign hosts has led to the development of a market in pieces of DNA known as expression vectors. Expression vectors, often but not invariably sold in the form of circular pieces of DNA known as plasmids, contain all of the genetic elements on them to express a protein coding sequence inserted into a defined location within the expression vector. Typically one would create the coding sequence for a protein that one wants to express and then insert that coding sequence into a defined location in the expression vector. The expression vector would already contain within it a promoter adapted for use in the host for which the expression vector is defined and may also include suitable downstream transcription terminators or polyadenylation sequences sufficient to terminate transcription, a necessary requirement in a eukaryotic, but not a prokaryotic host. Such expression vectors often would also have a selectable marker gene for one or more forms of antibiotic resistance so that the bacterial host containing the expression vector can readily be identified.

Different categories of host organisms require different promoters. For example, prokaryotic promoters such as those functional to cause gene expression in bacteria, are almost invariably non-functional in eukaryotic organisms such as vertebrate or plant cells or yeast. Even among eukaryotic organisms, most plant promoters do not work in animal cells and most animal promoters do not work in plant cells. Accordingly it is typically the case that an expression vector is designed for a specific host or class of hosts and has promoters and other genetic elements specifically designed for that specific host.

One prior vector is known that can be used in two hosts. The pDual vector from Stratagene includes promoters suitable for both mammalian cell expression and bacterial expression. No prior vector is known capable of operation in more than two categories of hosts.

BRIEF SUMMARY OF THE INVENTION

The present invention is summarized in that a multiple host expression vector has built within it a facility for expression of a inserted protein coding sequence in bacterial cells, vertebrate cells, and in baculovirus infected insect cells. This permits the same expression vector to be used in bacterial, insect, or vertebrate-cells to produce a protein of interest.

The vector of the present invention advantageously has diverse promoters in the orientation of vertebrate, then bacterial, then baculovirus, since then the bacterial and baculovirus promoters can be incorporated into 5' untranslated mRNA that does not affect efficient expression of an inserted gene sequence in vertebrate-cells.

The present invention is also summarized in that the p10 baculovirus promoter is used in such a multiple host expression vector, the p10 baculovirus promoter permitting high expression of inserted protein coding sequences in baculovirus infected insect cells without adversely effecting the functioning of other promoters contained within the vector.

Other objects, advantages and features of the present invention will become apparent from the following specification when taken in conjunction with the accompanying drawings.

DETAILED DESCRIPTION OF THE INVENTION

The present invention is characterized in that an expression vector is designed which is capable of efficient gene expression in bacterial, insect, and vertebrate host systems. This permits a user to insert a protein coding sequence at a single place within this expression vector and then to insert that same expression vector into a bacteria, into an insect cell in culture through a baculovirus, or into a vertebrate cell in culture, with the expression vector functional in all three of these hosts to produce the protein encoded by the protein coding sequence inserted in the vector. This permits transgenic expression in insect or vertebrate cells in order to obtain eukaryotic post-translational modification information on the protein of interest. At the same time the bacterial system can be used for initial studies to ascertain solubility or activity or to produce large amounts of protein for structural studies or antibody production. In this way the amount of genetic manipulations necessary to obtain high levels of expressed protein is minimized.

Figure 1:
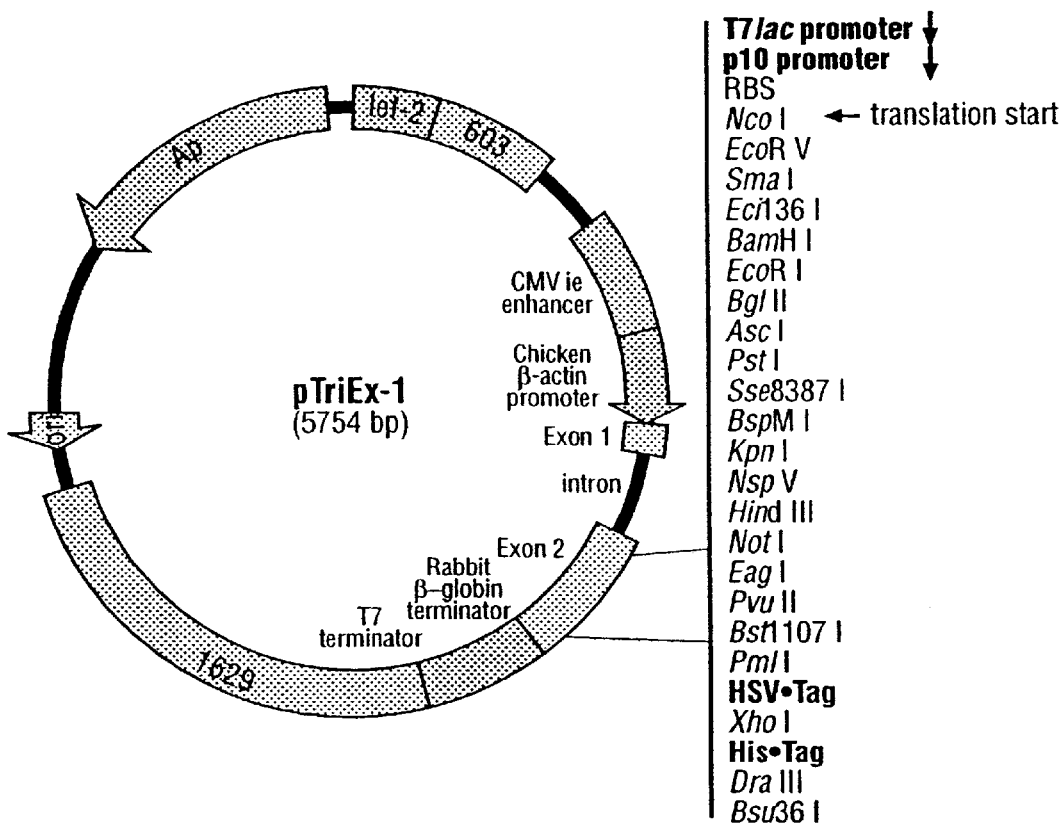
FIG. 1 is an illustration of a multiple host expression vector constructed in accordance with the present invention.

Shown in FIG. 1 is an exemplary multiple system expression vector designed for expression in three hosts. This vector, referred to here as the pTriEx-1 vector is a plasmid having multiple promoters all driving the expression of a protein coding sequence which can be inserted into a multiple cloning site illustrated in the figure. The plasmid includes provisions for three distinct types of promoters arranged so that the proper start of translation will occur regardless of which of the promoters initiates transcription. The promoter for expression in mammalian systems is a hybrid promoter created through a fusion of the chicken β-actin promoter with a 5' fusion of the cytomegalovirus immediate early enhancer sequence. The promoter chosen for expression in bacteria is the T7lac promoter, a tightly controlled promoter that is IPTG-inducible, which includes a bacteriophage T7 promoter just upstream of a lac repressor binding site (lacO). The promoter chosen for expression in insect cells is the p10 promoter, a late to very late promoter from the AcNPV baculovirus.

Figure 2:
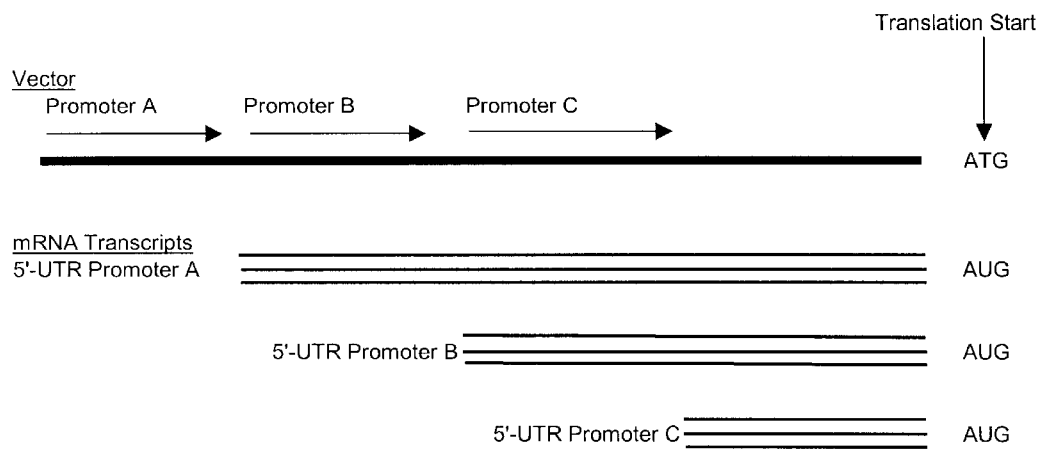
FIG. 2 is a conceptual illustration of the placement of promoters in the invention.
Figure 2:
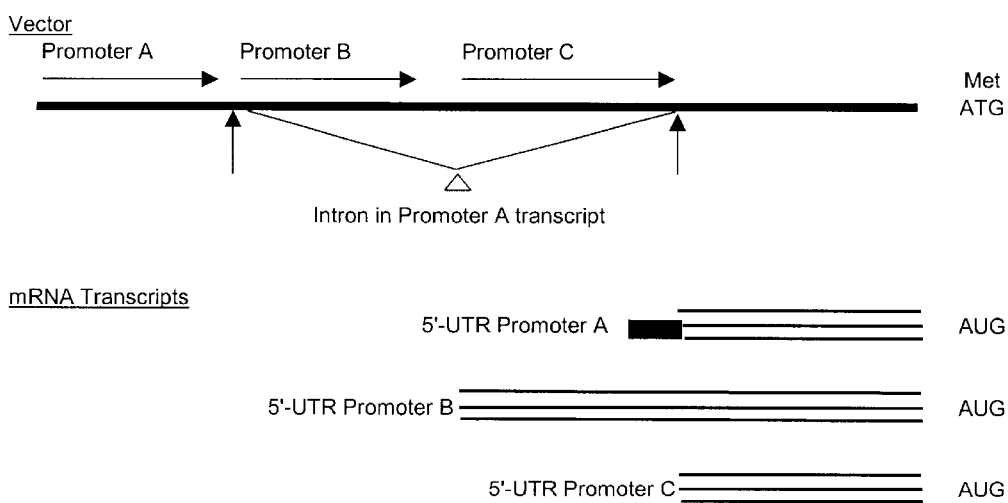

Of course, it is not just desirable in a triple host expression vector that the vector work in all three hosts, it is also desirable that the vector expresses proteins encoded by the inserted DNA well in all three hosts. This objective places constraints on the design of a vector. There must be promoter and enhancer elements appropriate for each host arranged on the vectors so as to be functional in each host without hindering the expression characteristics of the other hosts. There must be a translation initiation region that supports efficient initiation of the translation of the target protein in each of the hosts. One strategy is to place the promoters head to tail in tandem orientation, as suggested by FIG. 2. In that event, the promoter located at the 5' end of the promoter region would initiate transcription significantly upstream of the translation start site and the untranslated 5' region for the transcript it produces would include the downstream promoter sequences. It has been found that if the vertebrate promoter is placed at location A as the most upstream promoter, followed by the bacterial promoter which is followed in turn by the baculovirus insect promoter, all the promoters can work efficiently without any of them interfering with the expression of the others.

In addition to efficient and correct transcription, the vector must include sequences to initiate expression efficiently. The efficiency of translation is effected strongly in both E. coli and vertebrate cells by the nucleotide sequences that flank the start codon for the protein to be produced. In E. coli, the ATG (or AUG in the mRNA) start codon is typically 5–10 based downstream from a sequence known as the ribosome-binding site (RBS) or the Shine-Dalgarno sequence. The RBS sequence in the mRNA corresponds to all or part of the hexamer sequence AGGAGG, although few full-length consensus RBS sequences are found in nature. In addition to enhancing the efficiency of translation initiation, strong RBS sites also appear to enhance expression due to the ribosome-mediated protection of the mRNA from ribonuclease degradation and from rho-mediated transcription termination. For vertebrate cells, a consensus sequence from −6 to +4 known as the Kozak sequence has been shown to cause efficient translation initiation. The optimal context for this sequence is 5'-GCCRCCAUGG-3' (SEQ ID NO:2), where the AUG is the codon for the amino terminal methionine for the protein. Other than the start codon triplet itself, the nucleotides at −3, which must be R (meaning A or G) and +4 being a G have the largest role in determining translation efficiency.

In order for a triple host expression vector to be useful, it must express an inserted protein coding DNA sequence in all three hosts. To be most desirable and efficient, the vector must produce protein at levels commensurate with the results achieved with host specific vector systems. While it is perhaps reasonable to accept some diminution in quantity of protein produced by virtue of the fact that the vector works in three hosts, that diminution cannot be large or the vector will lose attractiveness compared to the less convenient alternative of using three host specific vectors. It is preferable if the results of using the triple host vector are at least as good as using alternative host specific vectors. Using the arrangement of promoters described above, it has been found that a triple host expression vector as described here produces results that are very commensurate with the results obtainable using host specific vectors, varying from slight less protein production to somewhat more protein production, depending on the protein produced, the host, and the host specific vector chosen. In any event, the triple host vector described here can clearly produce protein that is in the same order of magnitude of quantity as other comparable state of the art vectors which are specific to a given category of host.

The full DNA sequence of the pTriEx-1 vector is presented in SEQ ID NO:1 attached. Note that the site for protein initiation, ATG is nucleotides 2086–2088 of SEQ ID NO:1. The combined surrounding sequence, AAGGAGATATACCATGG, nucleotides 2073–2089 of SEQ ID NO:1, can serve as both a RBS site for prokaryotic expression and a Kozak sequence for vertebrate expression. The ATG itself is part of the Nco I site in the multiple cloning site which permits the insertion of protein coding sequences in frame into the vector.

The choice of promoter can also affect the efficiency of the multiple host range expression vector. For example, the choice of the preferred p10 promoter turns out to be superior to some baculovirus promoters in the triple host vector. The inventors here had first constructed a triple host expression vector, similar to pTriEx-1, but using a slightly modified polh baculovirus promoter. The polh promoter sequence was mutated to alter two upstream ATG sites that could potentially be associated with non-target protein translation initiation. In quantitative protein production experiments in insect cells in culture, the recombinant baculorvirus derived from the triple host vector with the mutant polh promoter produced protein at about 13% of the amount of protein produced in the same insect cells using a pBAC2cp derived baculovirus insect cell protein expression vector, which uses the wildtype polh promoter. By contrast, the recombinant baculorvirus derived from the pTriEx-1 vector described here, using the p 10 promoter, produced approximately 81% of the protein produced by insect cells infected with the pBAC2cp-derived baculorvirus vector.

The use of the triple host expression vector will vary slightly from host to host. For expression in a prokaryotic host, such as E. coli, the T7lac promoter is used. The T7 promoter transcripts are terminated at a downstream T7 terminator sequence indicated in FIG. 1. Expression of the target protein is accomplished by cloning DNA encoding the target protein into the multiple cloning site in the vector, taking care to see that the protein coding sequence is inserted in the open reading frame. The actual expression of the vector in the host is achieved by providing a source of T7 RNA polymerase. This can be done in any of several ways. The triple host expression vector can be inserted into a host not providing T7 RNA polymerase and then the host can be infected with a phage that expressed the polymerase. The triple host expression vector can also be transformed into a host which has been previously engineered to produce T7 polymerase, such as the Tuner (TM) (DE3)pLacI or Origami (TM) (DE3)pLacI hosts available from Novagen. Both of these hosts carry a chromosomal copy of the gene for T7 RNA polymerase under the control of the lacUV5 promoter and are lac repressed by a lacI gene on a plasmid. Each of these hosts can be induced to produce T7 RNA polymerase by IPTG.

For expression in insect cells using the triple host expression vector, one takes advantage of the segments of baculovirus DNA, open reading frames lef-2 and 603 and 1629, as shown in FIG. 1. Using these regions, recombinants can be generated by homologous recombination to make recombinant baculovirus. The baculovirus recombinants can then be used to infect insect cells using standard techniques. Expression of the target protein is conditioned by the late/ very late p10 promoter.

The expression of the pTriEx-1 promoter in vertebrate cells is driven by a constitutive promoter active in many cells types. This promoter is composed of the CMV immediate early enhancer sequence fused to the chicken β-actin promoter. The mRNA produced from this promoter contains an intron, a feature which is intended to facilitate mRNA processing and transport. Downstream of the multiple cloning site is a sequence for the rabbit β-globin terminator, which encodes an efficient polyadenylation site. The pTriEx-1 can be transformed by standard techniques into vertebrate cells or through the use of a recombinant baculovirus as the vector for delivery into the vertebrate cells.

The embodiment of the triple host expression vector of pTriEx-1 incorporates other useful features for gene cloning and protein expression and identification. The plasmid pTriEx-1 incorporates a multiple cloning site consisting of multiple adjacent restriction endonuclease cleavage sites that permit any blunt ended insert to be cloned into the vector in frame with any reading frame in the vector. This is done by providing overlapping sites for three restriction enzymes that leave blunt ends so that it is possible to create blunt ends that terminate at every position of a codon triplet.

Also, in pTriEx-1, inserts that lack an internal stop codon and that are in-frame will be expressed with two tagging proteins appended to the carboxyl end of the protein. The first tag adds an 11 amino acid epitope from Herpes simplex virus glycoprotein D to permit convenient detection of protein by Western blot using commercially available monoclonal antibody specific to that epitope. The second tag consists of a repeat of histidine residues which permits the protein produced from the vector to be rapidly purified by affinity separation using commercially available histidine binding resins.

There are other variants possible without departing from the present invention. Other promoters could be used as alternatives to the ones used in TriEx-1. For example, numerous other constitutive or inducible vertebrate promoters with or without associated enhancer elements are known that could be substitued for the present vertebrate promoter. Likewise other inducible *E. coli* promoters are known that could be substituted for the T7lac promoter. The present invention describes the use of a baculovirus derived promoter, however, it is also conceivable that the p10 promoter could be replaced by a known constitutive or inducible insect cell derived promoter. It also should be possible to substitute a plant or yeast promoter for one of the other promoter categories, in particular for the vertebrate promoter, to still achieve triple host range effectiveness. In fact, the results here are the first to demonstrate that three diverse promoters can all be used, in respective hosts, for expression of a common protein coding sequence. The three promoters could be chosen from any prokaryotic, insect, vertebrate, yeast or plant promoters.

It is also envisioned that there could be changes to replication origins in the vector to, for example, to broaden the bacterial host range of the vector. A eukaryotic replication origin could be added to facilitate episomal replication in vertebrate and/or yeast cells.

pTriEx-1 has regions which permit recombination with baculovirus DNA. It is also desirable under come circumstances to include recombination regions designed for other viruses or even into the chromosome of a target organism. It would be possible to use a triple host plasmid to make a polycistronic mRNA that permits the expression of more than one protein from a single transcript. Other affinity or purification tags could also be used to assist in protein detection or purification.

EXAMPLES

Figure 3:
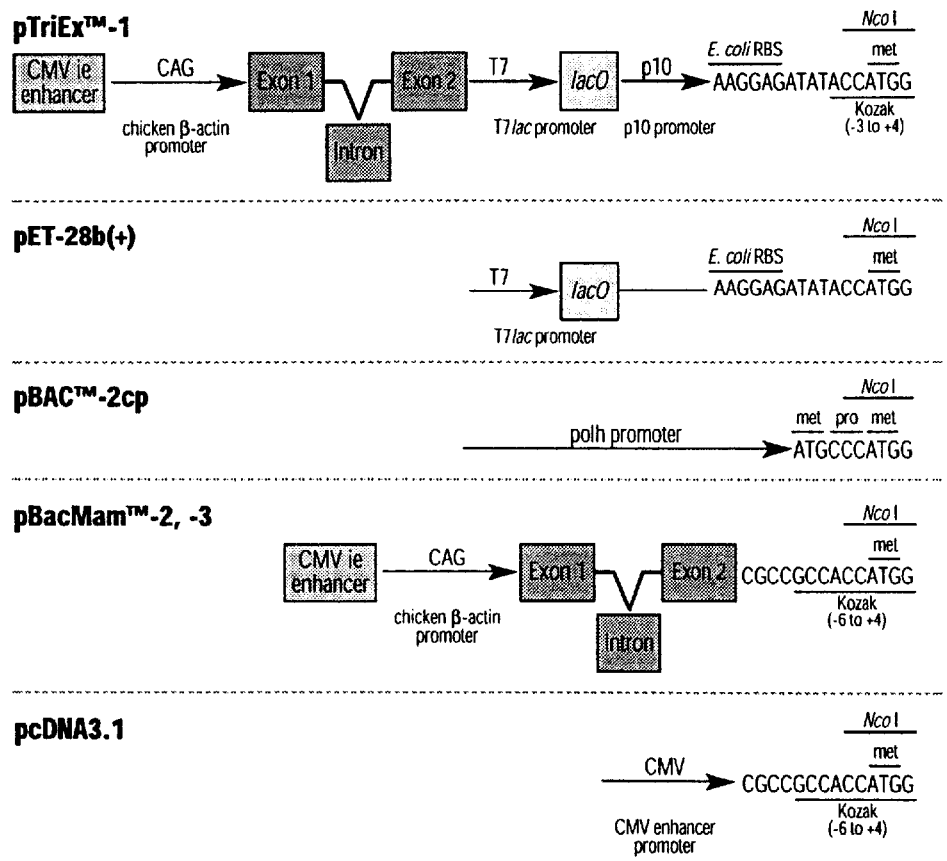
FIG. 3 is a schematic illustration which is a comparison of several of the promoter and translation regions contained in plasmids used in the examples below. The plasmid pTriEX™ is illustrated at the top of FIG. 3 and can also be found at SEQ ID NO:1 below. The DNA sequence at the end of pTriEx™-1 and pET-28b(+) is nucleotide 2073 to nucleotide 2089 of SEQ ID NO:1. The DNA sequence at the end of pBAC™-2cp is provided as SEQ ID NO:3 in the sequence listing. The DNA sequence at the end of pBacMam™-2, -3 and pcDNA3.1 is provided as SEQ ID NO:4 in the sequence listing.
Figure 4:
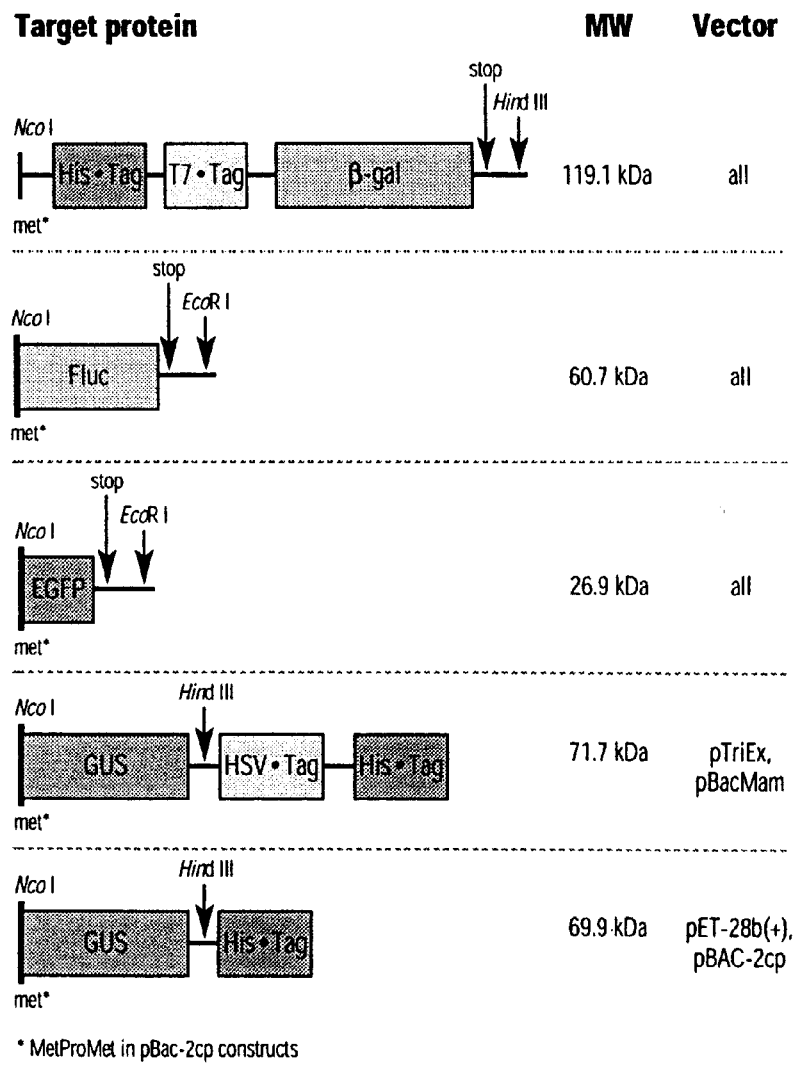
FIG. 4 is another schematic representation of the proteins used in the examples below.

In order to evaluate the performance of the triple host vector, the plasmid pTriEx-1 was tested and compared to host specific protein expression vectors. The reporter genes for the proteins β-galacosidase (β-gal), firefly luciferase (fluc), green flourescent protein (GLP) and β-glucuronidase (GUS) were cloned into copies of pTriEx-1, and also into the following host specific vectors: pET-28b(+) (an *E. coli* vector from Novagen), pBAC-2cp (a baculovirus vector from Novagen), pBacMam-2 and -3 (baculovirus, Novagen), pcDNA3.1 (mammalian, Invitrogen). FIG. 3 illustrates a comparison of the constructs in their promoter and translation initiation regions. FIG. 4 illustrates the target proteins and lists which vectors the coding sequences for the proteins were cloned into. In pTri-Ex-1, the inserts were directionally cloned into multiple cloning site in frame and the resulting vector was used. In pBacMan and pcDNA3.1, recombinants were created with linkers encoding a consensus Kozak sequence to provide a similar translation initiation site to pTriEx-1.

The expression of the proteins in pTriEx-1 and pET-28b (+) was evaluated in an *E. coli host*. The T7lac promoter, the RBS sequence and the translation initiation regions are identical between the two vectors. The primary differences between the vectors in this host are due to copy number and the method of inducing expression. Sufficient lac repressor is required when using the T7lac promoter in λDE3 lysogenic host strains to maintain repression of both the chromosomal promoter and the promoter on the plasmid. The plasmid pET-28b(+) is a low copy number plasmid and carries a lacI gene. In contrast, the plasmid pTriEx-1 is a high copy number plasmid that does not carry a lacI gene, and must be repressed by employing bacterial host strains which express sufficient lac repressor from a lacI gene present on a compatible plasmid or carried on the host chromosome.

The performance of pTriEx-1 was compared side-by-side with pET-28b(+). Recombinants were established in a Nova Blue (Novagen) host, a strain that lacks a source of T7 RNA polymerase. Verified recombinants were then transformed into host strains BL21(DE3) for pET-28b(+) and BL21 (DE3)pLacI for pTriEx-1, and protein induction accomplished by adding IPTG. The resulting proteins were suspended in 1×SDS buffer and size separated on a 4–20% SDS-PAGE electrophoresis gel. The gel was stained with Coomassie blue. For all four of the proteins, the visible bands from expression in pTriEx-1 were at least as intense as the comparable band produced from the pET28b(+) cultures. The only protein that did not expressed to high levels in either case was EGFP, a version of GFP which has been codon optimized for human codon preferences.

A corresponding test was conducted in insect cells. pTriEx-1 and pBAC-2cp recombinants were co-transfected with linearized BacVector-3000 DNA into Sf9 insect cells to generate vTriEx and vBAC-2cp based baculovirus recombinants. The primary functional differences between the vTriEx and vBAC-2cp recombinants are the promoters and the translation initiation regions. Both the p10 promoter and the polh promoter are known to be powerful late/very late baculovirus promoters, and would be expected to direct similar levels of protein expression. Previous work has demonstrated that the 5'-untranslated region of both the polh and the p10 mRNA contains a sequence element required for the burst of expression during the very late phase of infection. That region is also present in the polh promoter found in pBAC-2cp. The recombinant baculovirus were titered and used to infect Sf9 cells grown in shaker flasks in BacVector insect cell medium. Cells were harvested and total cell proteins recovered, suspended in 2×SDS, and run on 4–20% gels., followed by staining with Coomassie blue. The resulting gels revealed a comparable, or higher, level of expression from vTriEx-1 than in the cells infected with vBAC-2cp recombinants. In short, the triple host pTriEx-1 vector did just as well as, if not better than, the expression system specific vector in insect cells.

For vertebrate cells, the transfection was done by both traditional transfection techniques as well as a technique known as the BacMam method in which recombinant baculovirus encoding target genes under vertebrate promoters are used for transduction. The more traditional transfection methods are faster but the baculovirus method has low cytotoxicity and scales up more easily. To test plasmid based expression, pTriEx-1 was compared to the vectors pBacMam-2 and -3 as well as pcDNA3.1 . These vectors were not quite identical to TriEx-1 due to differences in choice of promoter and terminator, but the optimal Kozak consensus sequence was added to each in the cloning process so that they would be comparable in that feature.

Figure 5:
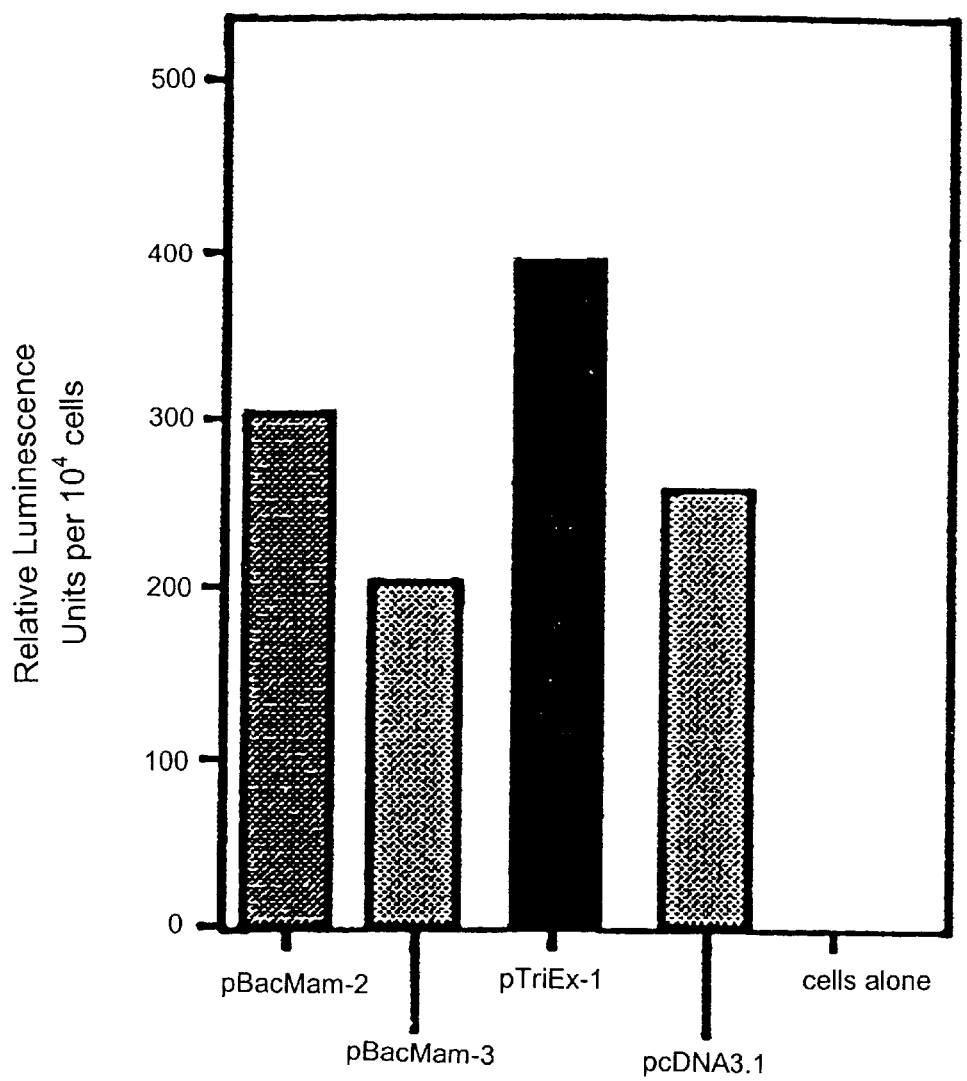
FIG. 5 is a histogram presenting some of the data from the examples below.

Using a traditional transfection technique, copies of pTriEx-1, pBacMam and pcDNA3.1 recombinants with a luciferase coding sequence inserted were transfected into COS-7 cells and cell lysates tested for luciferase activity after 24 hours of identical culture. The results are summarized in the histogram of FIG. 5. These results shown that for this gene and this host, the levels obtained from pTriEx-1 were at a minimum comparable to the results obtainable with pBacMam and pcDNA3.1. This demonstrates that the insertion of the T7lac promoter and the p10 promoter into the untranslated 5' region of the mRNA transcript made by the mammalian promote is not deleterious to the level of protein production in pTriEx-1.

Figure 6:
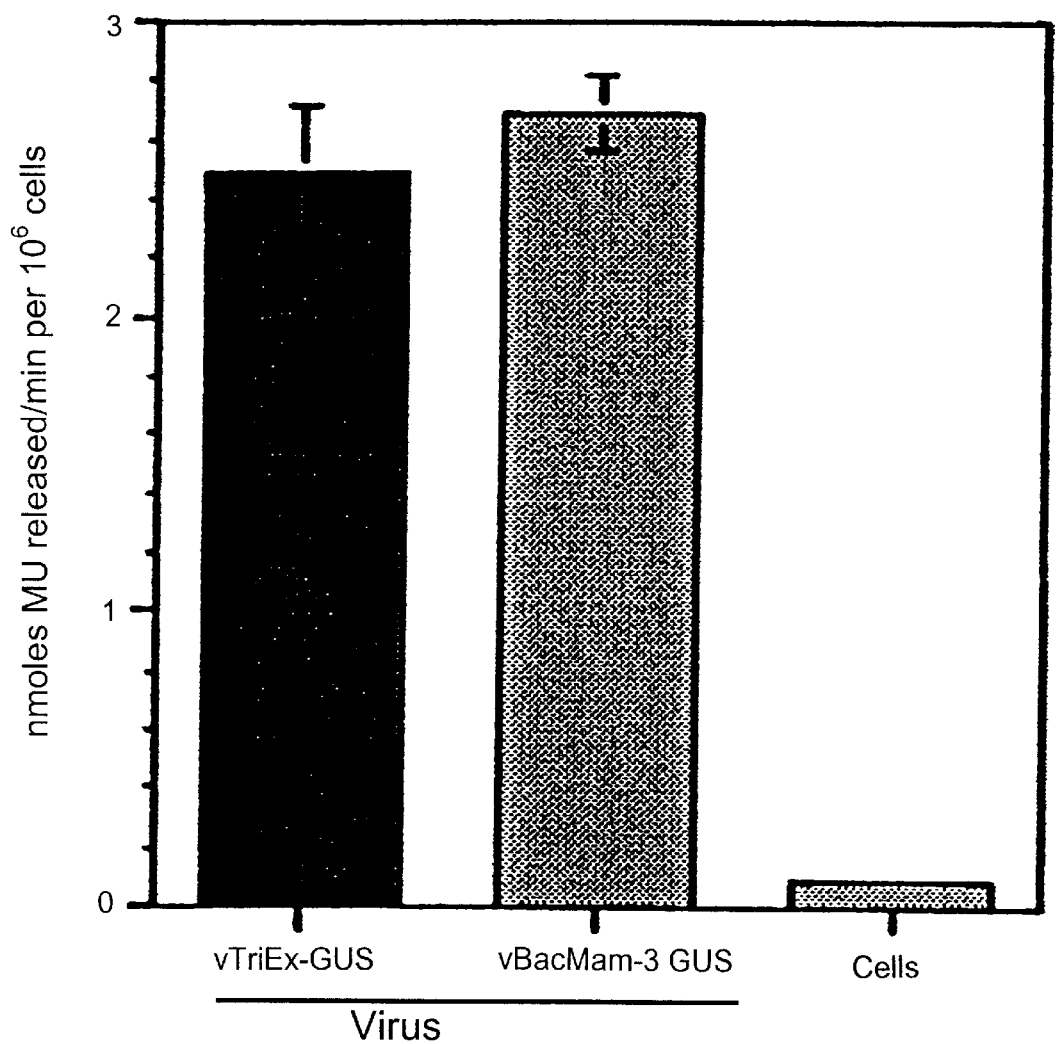
FIG. 6 is another histogram presenting more data from the examples below.

To further test expression in mammalian cells, the vTriEx and vBacMam recombinant baculovirus containing the GUS gene were used to transduce COS-7 cells at 100–200 MOI per cell. Cell lysates were tested for expressed GUS activity after 24 hours. The results are presented in the histogram of FIG. 6. The levels of activity evidenced by the two cultures were comparable.

We claim:

1. A vector for expressing a protein in three separate host cells, the vector comprising three separate promoters, wherein the first promoter is effective to express a downstream protein coding sequence in one type of host cell, the second promoter is effective to express the downstream protein coding sequence in a second different type of host cell, and the third promoter is effective to express the downstream protein coding sequence in a third different type of host cell, where the hosts are any combination of three selected from the group consisting of prokaryotic, insect, vertebrate, plant and yeast cells;

a multiple cloning site downstream of the promoters such that a protein coding sequence inserted into the multiple cloning site is transcribed by one of the three promoters in each of the three different types of host cells; and at least two transcriptional terminators located downstream of the multiple cloning site to terminate transcription of the promoters, one transcriptional terminator effective in bacterial cells and the other effective in eukaryotic cells.

2. A vector for expressing a protein in bacterial, vertebrate and insect host cells, the vector comprising three separate promoters, wherein one promoter is effective to express a downstream protein coding sequence in vertebrate host cells, a second promoter is effective to express the downstream protein coding sequence in bacterial host cell, and a third promoter is effective to express the downstream protein coding sequence in insect host cells wherein the promoter effective to express the downstream protein coding sequence in insect host cells is the baculovirus p10 promoter;

a multiple cloning site downstream of the promoters such that a protein coding sequence inserted into the multiple cloning site is transcribed by one of the three promoters in each of the three different types of host cells; and at least two transcriptional terminators located downstream of the multiple cloning site to terminate transcription of the promoters, one transcriptional terminator effective in bacterial cells and the other effective in eukaryotic cells.

3. The vector as claimed in claim 2 wherein the vector further comprises a consensus ribosome binding site and Kozak sequence including the following DNA sequence: AAGGAGATATACCATGG (base pairs 2073 to 2089 of SEQ ID NO:1).

4. The vector as claimed in claim 2 wherein the promoter effective to express the downstream protein coding sequence in vertebrate host cells includes the cytomegalovirus immediate early enhancer combined with the chicken β-actin promoter.

5. The vector as claimed in claim 2 wherein the promoter effective to express the downstream protein coding sequence in bacterial host cells is the T7lac inducible promoter.

6. A vector for expressing a protein in vertebrate, bacterial and insect host cells, the vector comprising 5' to 3':

a promoter effective in vertebrate cells;

a bacteriophage promoter effective in bacterial cells;

a baculovirus promoter effective in insect cells, the promoters arranged so that the transcript made by the vertebrate promoter includes the region of the bacterial and the baculovirus promoters;

a multiple cloning site for insertion of a protein coding sequence for a target protein;

a transcriptional termination sequence effective in eukaryotic cells; and a transcriptional termination sequence effective in bacterial cells.

7. The vector as claimed in claim 5 wherein the vector further comprises a consensus ribosome binding site and Kozak sequence including the following DNA sequence: AAGGAGATATACCATGG (base pairs 2073 to 2089 of SEQ ID NO:1).

8. The vector as claimed in claim 6 wherein the baculovirus promoter is the p10 promoter.

9. A vector having the DNA sequence of SEQ ID NO:1.

* * * * *